US008682001B2

(12) United States Patent
Annunziato et al.

(10) Patent No.: US 8,682,001 B2
(45) Date of Patent: Mar. 25, 2014

(54) IN-EAR ACTIVE NOISE REDUCTION EARPHONE

(71) Applicant: Bose Corporation, Framingham, MA (US)

(72) Inventors: Kevin P. Annunziato, Medway, MA (US); Jason Harlow, Watertown, MA (US); Michael Monahan, Southborough, MA (US); Anand Parthasarathi, Ashland, MA (US); Ryan C. Silvestri, Franklin, MA (US); Eric M. Wallace, Chelmsford, MA (US)

(73) Assignee: Bose Corporation, Framingham, MA (US)

( * ) Notice: Subject to any disclaimer, the term of this patent is extended or adjusted under 35 U.S.C. 154(b) by 0 days.

(21) Appl. No.: 13/864,865

(22) Filed: Apr. 17, 2013

(65) Prior Publication Data

US 2013/0315412 A1 Nov. 28, 2013

Related U.S. Application Data

(63) Continuation of application No. 13/480,766, filed on May 25, 2012.

(51) Int. Cl.
*G10K 11/16* (2006.01)
*H03B 29/00* (2006.01)
*A61F 11/06* (2006.01)

(52) U.S. Cl.
USPC ....................................... 381/71.8; 381/71.12

(58) Field of Classification Search
USPC ............... 381/71, 72, 83, 93, 96, 71.8, 71.12, 381/71.1; 700/94
See application file for complete search history.

(56) References Cited

U.S. PATENT DOCUMENTS

| | | | | |
|---|---|---|---|---|
| 4,985,925 | A | 1/1991 | Langberg et al. | |
| 6,567,524 | B1 | 5/2003 | Svean et al. | |
| 6,683,965 | B1 | 1/2004 | Sapiejewski | |
| 7,039,195 | B1 | 5/2006 | Svean et al. | |
| 7,289,636 | B2 | 10/2007 | Saunders et al. | |
| 7,916,888 | B2 | 3/2011 | Sapiejewski et al. | |
| 8,385,560 | B2 * | 2/2013 | Solbeck et al. | 381/71.8 |
| 2006/0120545 | A1 * | 6/2006 | Rasmussen | 381/312 |
| 2009/0080670 | A1 * | 3/2009 | Solbeck et al. | 381/71.6 |
| 2011/0044464 | A1 | 2/2011 | Sapiejewski et al. | |
| 2012/0215519 | A1 * | 8/2012 | Park et al. | 704/2 |
| 2013/0058493 | A1 | 3/2013 | Darlington et al. | |

* cited by examiner

*Primary Examiner* — Fan Tsang
*Assistant Examiner* — Eugene Zhao

(57) ABSTRACT

An active noise reduction earphone. The earphone includes structure for positioning and retaining the earphone in the ear of a user without a headband, active noise reduction circuitry including an acoustic driver with a nominal diameter greater than 10 mm oriented so that a line parallel to, or coincident with, an axis of the acoustic driver and that intersects a centerline of the nozzle intersects the centerline of the nozzle at angle $\theta > \pm 30$ degrees. A microphone is positioned adjacent an edge of the acoustic driver. The earphone is configured so that a portion of the acoustic driver is within the concha of a user and another portion of the acoustic driver is outside the concha of the user when the earphone is in position. An opening coupling the nozzle to the environment includes impedance providing structure in the opening.

26 Claims, 12 Drawing Sheets

Fig. 8E
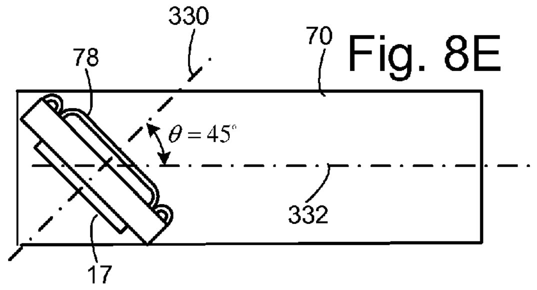
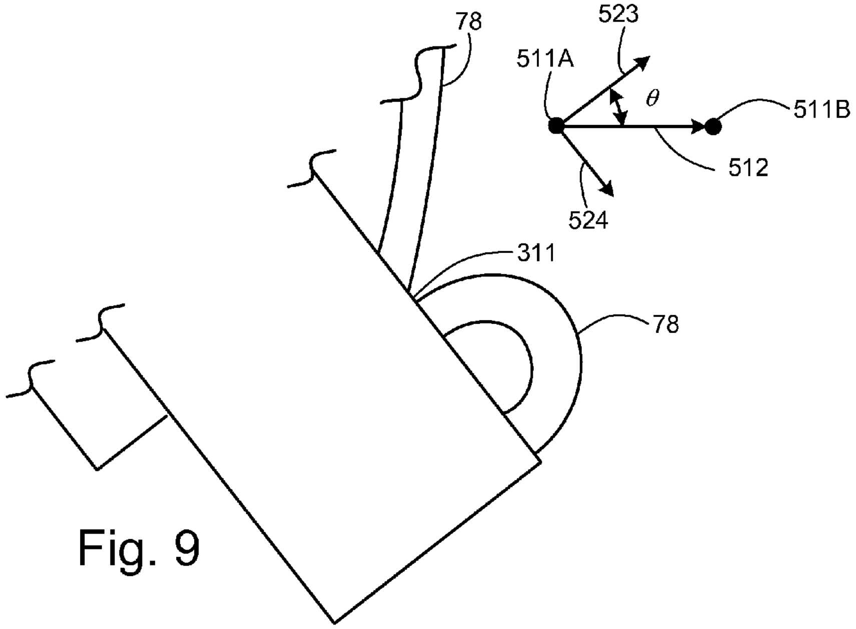
Fig. 9

Fig. 12A
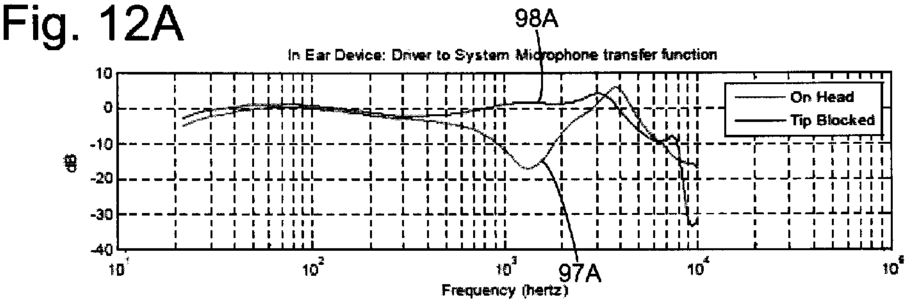
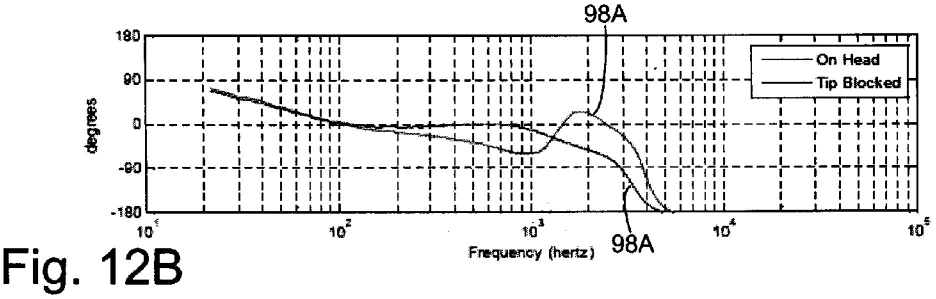
Fig. 12B
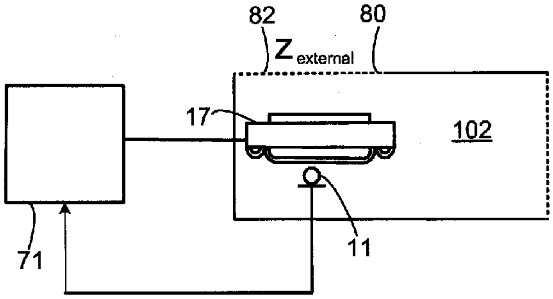
Fig. 13A
Fig. 13B
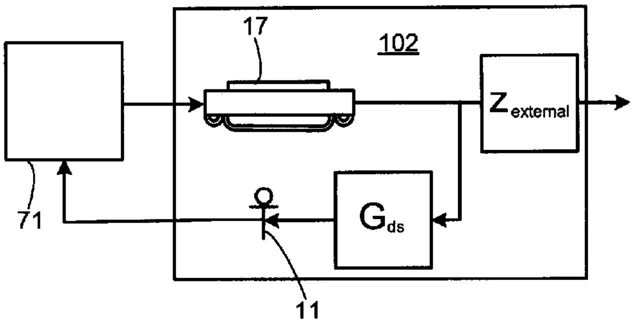

IN-EAR ACTIVE NOISE REDUCTION EARPHONE

PRIORITY CLAIM

This application is a continuation of U.S. patent application Ser. No. 13/480,766, filed May 24, 2012, the entire contents of which are incorporated here by reference.

BACKGROUND

This specification describes an in-ear active noise reduction (ANR) earphone. Active noise reduction earphones are discussed in U.S. Pat. No. 4,455,675. In-ear earphones are designed to be used with all, or a significant portion of the earphone in the ear of the user. In-ear earphones typically have a portion that is in the ear canal of a user when the earphone is in position.

SUMMARY

In one aspect, an earphone includes an earphone. The earphone includes a nozzle sealing with the entrance to the ear canal to form a cavity, the cavity including a sealed portion of an ear canal and a passageway in the nozzle. The earphone further includes a feedback microphone, for detecting noise in the cavity and feedback circuitry, responsive to the feedback microphone, for providing a feedback noise canceling audio signal. The earphone further includes an acoustic driver for transducing an output noise canceling audio signal includes the feedback noise canceling audio signal to acoustic energy that attenuates the noise, an opening coupling the cavity to the environment, and impedance-providing structure in the opening. The impedance-providing structure may include an acoustically resistive material in the opening. The acoustically resistive material may be wire mesh. The impedance-providing structure may include a tube acoustically coupling the opening and the environment. The tube may be filled with foam. The cavity and the eardrum of a user may be characterized by an impedance z and the absolute value of the impedance of the impedance-providing structure may be less than the absolute value of z at frequencies lower than a predetermined frequency and higher than the absolute value of z at frequencies higher than the predetermined frequency. The earphone may further include structure for engaging the outer ear so that the earphone is positioned and retained in the ear of a user without the use of a headband. The passageway may have an open cross sectional area of greater than 13 $mm^2$. The acoustic driver may be oriented so that a line parallel to, or coincident with, the axis of the acoustic driver and that intersects a centerline of the nozzle intersects the centerline of the nozzle at angle $\theta$>30 degrees. The nozzle may have a ratio $$\frac{l}{A}$$

of $$1000\frac{\text{m}}{\text{m}^2}$$

or less, wherein A is the open cross sectional area of the nozzle and l is the length of the nozzle. The nozzle may have an acoustic mass M of $$1200\frac{\text{kg}}{\text{m}^4}$$

or less where $$M = \frac{\rho l}{A},$$

$\rho$ is the density of air, A is the open cross sectional area of the nozzle, and l is the length of the nozzle. The absolute value of the mass impedance |z| of the passageway may be $8.0\times10^6$ $$\frac{\text{kg}}{\text{m}^4 sec}$$

or less at 1 kHz, where |z|=Mf, where $$M = \frac{\rho l}{A},$$

$\rho$ is the density of air, A is the open cross sectional area of the passageway, l is the length of the passageway, and f is the frequency. The earphone my further includes a feed forward microphone, for detecting noise external to the earphone; feed forward circuitry, responsive to the feed forward microphone, for providing a feed forward noise reduction audio signal; circuitry for combining the feedback noise reduction audio signal and the feed forward noise reduction audio signal to provide the output noise reduction audio signal.

In another aspect, an earphone includes an earphone. The earphone includes a cavity that includes an ear canal of a user. The earphone may further include a feedback microphone, for detecting noise in the cavity, and feedback circuitry, responsive to the feedback microphone, for providing a feedback noise canceling audio signal. The earphone further includes an acoustic driver for transducing an output noise reduction audio signal that includes the feedback noise reduction audio signal to acoustic energy and radiating the acoustic energy into the cavity to attenuate the noise. The earphone may further include an opening coupling the cavity and the environment and impedance-providing structure in the opening. The impedance-providing structure may include acoustically resistive material in the opening. The impedance-providing structure may further include a tube acoustically coupling the opening and the environment. The tube may be filled with foam. The cavity and the eardrum of a user may define an impedance z and the absolute value of the impedance of the impedance-providing structure may be less than the absolute value of z at frequencies lower than a predetermined frequency and higher than the absolute value of the z at frequencies higher than the predetermined frequency. The cavity may further include a passageway acoustically coupled to the ear canal and sealing structure, for acoustically sealing the cavity from the environment. The earphone may further includes a feed forward microphone, for detecting noise external to the earphone; feed forward circuitry, responsive to the feed forward microphone, for providing a feed forward noise canceling audio signal, and circuitry for combining the feed forward noise canceling audio signal and the feedback noise canceling audio signal to provide the output noise canceling audio signal.

In another aspect, an earphone includes a cavity that includes an ear canal of a user; a feedback microphone, for detecting noise in the cavity; feedback circuitry, responsive to the feedback microphone, for providing a feedback noise canceling audio signal; an acoustic driver for transducing an output noise canceling audio signal includes the feedback noise canceling audio signal to acoustic energy and radiating the acoustic energy into the cavity to attenuate the detected noise; and an acoustical shunt coupling the cavity and the environment and providing an acoustical impedance between the cavity and the environment. The shunt may include a passageway and acoustical damping material in the passageway. The shunt may include an opening between the cavity and the environment and acoustically resistive mesh in the opening. The shunt may include one of holes in the shell of the earphone. The shunt may include an insert with holes formed in the insert. The earphone may further include a feed forward microphone, for detecting noise outside the earphone; feed forward circuitry, responsive to the feed forward microphone, for providing a feed forward noise canceling audio signal; and circuitry for combining the feedback noise canceling audio signal and the feed forward noise canceling audio signal to provide the output noise canceling audio signal.

In another aspect, an earphone includes an active noise reduction (ANR) earphone. The ANR earphone includes ANR circuitry comprising a feedback microphone acoustically coupled to an ear canal of a user, for detecting noise; feedback circuitry, responsive to the feedback microphone, for providing a feedback noise cancelling audio signal; and an acoustic driver for transducing an output noise canceling audio signal comprising the feedback noise reduction audio signal. The earphone further includes a passageway acoustically coupling the acoustic driver and an ear canal of a user. The acoustic driver is oriented so that a line parallel to, or coincident with, an axis of the acoustic driver and that intersects a centerline of the passageway intersects the centerline of the passageway at angle θ>±30 degrees. The microphone is radially positioned between a point of attachment of a voice coil to an acoustic driver diaphragm and an edge of the acoustic driver diaphragm. The passageway has a ratio $$\frac{l}{A}$$

of $$1000\frac{\mathrm{m}}{\mathrm{m}^2}$$

or less, where A is the open cross sectional area of the passageway and l is the length of the passageway. The passageway acoustically seals with the ear canal at the transition between the bowl of the concha and the entrance to the ear canal to form a cavity. The acoustic mass M of the passageway is $$1200\frac{\mathrm{kg}}{\mathrm{m}^4}$$

or less, where $$M = \frac{\rho l}{A},$$

ρ is the density of air, A is the open cross sectional area of the passageway and l is the length of the passageway. The absolute value of the mass impedance |z| of the passageway is $$800\times10^3\frac{kg}{m^4sec}$$

or less at 100 Hz and $$8.0\times10^6\frac{kg}{m^4sec}$$

or less at 1 kHz, where |z|=Mf, where $$M = \frac{\rho l}{A},$$

ρ is the density of air, A is the open cross sectional area of the passageway and l is the length of the passageway. The earphone may further include structure engaging the outer ear for positioning and retaining the earphone in the ear. The angle θ> may be ±45 degrees. The earphone may further include an opening coupling the cavity to the environment and impedance-providing structure in the opening. The impedance-providing structure may include an acoustically resistive material in the opening. The acoustically resistive material may be wire mesh. The acoustically resistive material may include a plastic member with holes therethrough. The impedance-providing structure may include a tube acoustically coupling the opening and the environment. The tube may be filled with foam. The acoustic driver may have a nominal diameter of greater than 10 mm. The acoustic driver may have a nominal diameter of greater than 14 mm. The earphone may be configured so that a portion of the acoustic driver is within the concha of a user and another portion of the acoustic driver is outside the concha of the user when the earphone is in position. The earphone may further include a feed forward microphone, for detecting noise outside the earphone; feed forward circuitry, responsive to the feed forward microphone, for providing a feed forward noise canceling audio signal; and circuitry for combining the feedback noise canceling audio signal and the feed forward noise canceling audio signal to provide the output noise canceling audio signal. The density of air ρ may be assumed to be $$1.2\frac{kg}{m^3}.$$

In another aspect, an earphone includes an active noise reduction (ANR) earphone. The ANR earphone includes structure for engaging the outer ear so that the earphone is positioned and retained in the ear of a user; active noise reduction circuitry comprising a feedback microphone acoustically coupled to an ear canal of a user, for detecting noise; feedback circuitry, responsive to the feedback microphone, for providing a feedback noise cancelling audio signal; and an acoustic driver with a nominal diameter greater than 10 mm for transducing an output noise canceling audio signal comprising the feedback noise canceling audio signal to attenuate the noise. The earphone further includes a passageway acoustically coupling the acoustic driver with the ear canal of a user at the transition between the bowl of the concha and the entrance to the ear canal. The earphone is configured so that a portion of the acoustic driver is within the concha of a user and another portion of the acoustic driver is outside the concha of the user when the earphone is in position. The acoustic driver may be oriented so that a line parallel to, or coincident with, an axis of the acoustic driver and that intersects a centerline of the nozzle intersects the centerline of the nozzle at angle θ>±30 degrees.

In another aspect, an earphone includes an active noise reduction (ANR) earphone. The ANR earphone includes structure for engaging the outer ear so that the earphone is positioned and retained in the ear of a user; structure for sealing the earphone with the ear canal at the transition between the bowl of the concha and the entrance to the ear canal; active noise reduction circuitry comprising a feedback microphone acoustically coupled to an ear canal of a user, for detecting noise inside the earphone; feedback circuitry, responsive to the feedback microphone for providing a feedback noise cancelling audio signal; and an acoustic driver for transducing an output noise canceling audio signal comprising the feedback noise canceling audio signal to noise canceling acoustic energy. The earphone further includes a passageway acoustically coupling the acoustic driver and an ear canal of a user. The passageway has a length l and an open cross sectional area A, and wherein the ratio $$\frac{l}{A}$$

is $$1000\frac{\text{m}}{\text{m}^2}$$

or less. The ratio $$\frac{l}{A}$$

may be $$900\frac{\text{m}}{\text{m}^2}$$

or less. The nozzle may have an open cross sectional area of greater than 10 $\text{mm}^2$ and a length of less than 14 mm. The nozzle may have a rigid portion and a compliant portion. The nozzle may include a frusto-conically shaped structure for engaging the area of transition between the ear canal and the bowl of the concha and acoustically sealing the ear canal with the nozzle.

In another aspect, an earphone includes an earphone for an active noise reduction (ANR) earphone. The active noise reduction earphone includes structure for engaging the outer ear so that the earphone is positioned and retained in the ear of a user; structure for sealing the earphone with an ear canal of a user; active noise reduction circuitry comprising a feedback microphone acoustically coupled to the ear canal, for detecting noise in the earphone; feedback circuitry responsive to the feedback microphone for providing a feedback noise cancelling audio signal; and an acoustic driver for transducing an output noise canceling audio signal comprising the feedback noise canceling audio signal to noise canceling acoustic energy. The earphone further includes a passageway acoustically coupling the acoustic driver and an ear canal of a user. The passageway has an open cross sectional area of at least 10 $\text{mm}^2$. The earphone nozzle may have a ratio $$\frac{l}{A}$$

of $$1000\frac{\text{m}}{\text{m}^2}$$

or less, wherein A is the open cross sectional area of the passageway and l is the length of the passageway. The passageway may acoustically seal with the ear canal at the transition between the bowl of the concha and the entrance to the ear canal to form a cavity. The acoustic driver may be oriented so that a line parallel to, or coincident with, an axis of the acoustic driver and that intersects a centerline of the passageway intersects the centerline of the passageway at angle θ>±30 degrees. The acoustic driver may have a nominal diameter of greater than 10 mm. The absolute value of the mass impedance |z| of the passageway may be $800\times10^3$ or less at 100 Hz and $8.0\times10^6$ or less at 1 kHz. The passageway may have an acoustic mass M of $$1200\frac{\text{kg}}{\text{m}^4}$$

or less, where $$1.2\frac{kg}{m^3}.$$

ρ is the density of air, A is the open cross sectional area of the passageway and l is the length of the passageway. The density of air ρ may be assumed to be $$1.2\ \frac{\text{kg}}{m^3}.$$

In another aspect, an earphone includes an active noise reduction (ANR) earphone. The ANR earphone includes structure for engaging the outer ear so that the earphone is positioned and retained in the ear of a user without the use of a headband; active noise reduction circuitry comprising an acoustic driver with a nominal diameter greater than 10 mm; a feedback microphone acoustically coupled to an ear canal of a user, for detecting noise in the earphone; feedback circuitry responsive to the feedback microphone for providing a feedback noise canceling audio signal; and an acoustic driver for transducing an output noise canceling audio signal comprising the feedback noise canceling audio signal to noise canceling acoustic energy. The earphone may further include a passageway acoustically coupling the acoustic driver and an ear canal of a user. The acoustic driver may be oriented so that a line parallel to, or coincident with, an axis of the acoustic driver and that intersects a centerline of the passageway intersects the centerline of the passageway at angle θ>±30 degrees. The acoustic driver may be oriented so that a line parallel to, or coincident with, an axis of the acoustic driver and that intersects a centerline of the passageway intersects the centerline of the nozzle at angle θ>±45 degrees. The microphone may be radially positioned intermediate a point at which an acoustic driver diaphragm is attached to an acoustic driver voice coil and an edge of the diaphragm. The microphone may be positioned at the intersection of an acoustic driver module and the passageway. A portion of the acoustic driver may be outside the concha when the earphone is in position.

In another aspect, an active noise reduction (ANR) earphone includes structure for engaging the outer ear so that the earphone is positioned and retained in the ear of a user; active noise reduction circuitry comprising an acoustic driver with a nominal diameter greater than 10 mm; a feedback microphone acoustically coupled to an ear canal of a user, for detecting noise in the earphone; feedback circuitry responsive to the feedback microphone for providing a feedback noise canceling audio signal; and an acoustic driver for transducing an output noise canceling audio signal. The noise canceling audio signal may include the feedback noise canceling audio signal to noise canceling acoustic energy. The earphone may further include a passageway acoustically coupling the acoustic driver and an ear canal of a user. The passageway may have a mass impedance |z| of $$8.0\times10^{6}\ \frac{\text{kg}}{m^4\ \text{sec}}$$

or less at 1 kHz, where |z|=Mf, where $$M=\frac{\rho l}{A},$$

ρ is the density of air, A is the open cross sectional area of the passageway and l is the length of the passageway. The absolute value of the mass impedance |z| of the passageway may be $$800\times10^{3}\ \frac{\text{kg}}{m^4\ \text{sec}}$$

or less at 1 kHz. The density of air ρ may be assumed to be $$1.2\ \frac{\text{kg}}{m^3}.$$

In another aspect, an earphone includes an active noise reduction (ANR) earphone. The ANR earphone includes structure for engaging the outer ear so that the earphone is positioned and retained in the ear of a user; active noise reduction circuitry comprising an acoustic driver with a nominal diameter greater than 10 mm; a feedback microphone acoustically coupled to an ear canal of a user, for detecting noise in the earphone; feedback circuitry responsive to the feedback microphone for providing a feedback noise canceling audio signal; and an acoustic driver for transducing an output noise canceling audio signal that includes the feedback noise canceling audio signal to noise canceling acoustic energy. The earphone further includes a passageway acoustically coupling the acoustic driver and an ear canal of a user. The passageway has an acoustic mass $$M\ \text{of}\ 1200\ \frac{\text{kg}}{m^4}$$

or less, where $$M=\frac{\rho l}{A},$$

ρ is the density of air, A is the open cross sectional area of the passageway and l is the length of the passageway. The density of air ρ may be assumed to be $$1.2\ \frac{\text{kg}}{m^3}.$$

The passageway may have an acoustic mass M of $$1100\ \frac{\text{kg}}{m^4}$$

or less, where $$M=\frac{\rho l}{A},$$

ρ is the density of air, A is the open cross sectional area of the passageway and l is the length of the passageway.

In another aspect, an earphone includes an active noise reduction (ANR) earphone. The ANR earphone includes structure for retaining the earphone in position in an ear without a headband and active noise reduction circuitry. The active noise reduction circuitry includes a feedback microphone acoustically coupled to an ear canal of a user, for detecting noise in the earphone; feedback circuitry responsive to the feedback microphone for providing a feedback noise canceling audio signal; a feed forward microphone, for detecting noise outside the earphone; feed forward circuitry, responsive to the feed forward microphone, for providing a feed forward noise canceling audio signal; and circuitry for combining the feedback noise canceling audio signal and the feed forward noise canceling audio signal to provide an output noise canceling audio signal; an acoustic driver for transducing an output noise canceling audio signal comprising the feedback noise reduction audio signal. The earphone includes a passageway acoustically coupling the acoustic driver and an ear canal of a user. The passageway has an open cross sectional area of 7.5 mm or greater. The passageway may have an open cross sectional area of 10.mm or greater Other features, objects, and advantages will become apparent from the following detailed description, when read in connection with the following drawing, in which:

BRIEF DESCRIPTION OF THE SEVERAL VIEWS OF THE DRAWING

FIGS. 8A-8E are diagrammatic views of earphones;

FIG. 9 is a diagrammatic partial cross sectional view of an acoustic driver and a microphone;

FIGS. 12A and 12B are plots of amplitude and phase, respectively, vs. frequency;

FIGS. 13A and 13B are diagrammatic views of earphone configurations;

DETAILED DESCRIPTION

Figure 1:
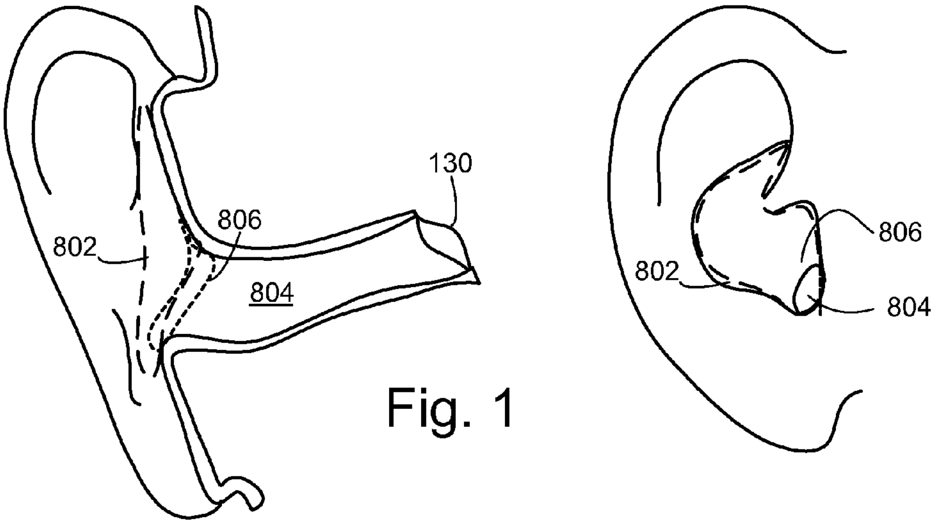
FIG. 1 is a front cross sectional view and a lateral view of an ear.

Though the elements of several views of the drawing may be shown and described as discrete elements in a block diagram and may be referred to as "circuitry", unless otherwise indicated, the elements may be implemented as one of, or a combination of, analog circuitry, digital circuitry, or one or more microprocessors executing software instructions. The software instructions may include digital signal processing (DSP) instructions. Operations may be performed by analog circuitry or by a microprocessor executing software that performs the mathematical or logical equivalent to the analog operation. Unless otherwise indicated, signal lines may be implemented as discrete analog or digital signal lines, as a single discrete digital signal line with appropriate signal processing to process separate streams of audio signals, or as elements of a wireless communication system. Some of the processes may be described in block diagrams. The activities that are performed in each block may be performed by one element or by a plurality of elements, and may be separated in time. The elements that perform the activities of a block may be physically separated. Unless otherwise indicated, audio signals or video signals or both may be encoded and transmitted in either digital or analog form; conventional digital-to-analog or analog-to-digital converters may not be shown in the figures.

"Earphone" as used herein refers to a device that fits around, on, or in an ear and which radiates acoustic energy into the ear canal. An earphone may include an acoustic driver to transduce audio signals to acoustic energy. While the figures and descriptions following use a single earphone, an earphone may be a single standalone unit or one of a pair of earphones, one for each ear. An earphone may be connected mechanically to another earphone, for example by a headband or by leads which conduct audio signals to an acoustic driver in the earphone. An earphone may include components for wirelessly receiving audio signals. Unless otherwise specified, an earphone may include components of an active noise reduction (ANR) system, which will be described below.

"Nominal" as used herein with respect to a dimension, refers to the dimension as specified by a manufacturer in, for example, a product specification sheet. The actual dimension may differ slightly from the nominal dimension.

FIG. 1 shows a front cross section and a lateral view of an ear for the purpose of explaining some terminology used in this application. For clarity, the tragus, a feature which in many people partially or completely obscures in the lateral view the entrance to the ear canal, is omitted. The concha is an irregularly bowl shaped region of the ear enclosed generally by dashed line 802. The ear canal 804 is an irregularly shaped cylinder with a non-straight centerline coupling the concha with the eardrum 130. Because the specific anatomy of ears varies widely from individual to individual, and because the precise boundaries between anatomical parts of the ear are not well defined, it may be difficult to describe some ear elements precisely. Therefore, the specification may refer to a transition area, enclosed generally by line 806, between the bowl of the concha and the ear canal. The transition area may include a portion of the ear canal or a portion of the bowl of the concha, or both.

Figure 2:
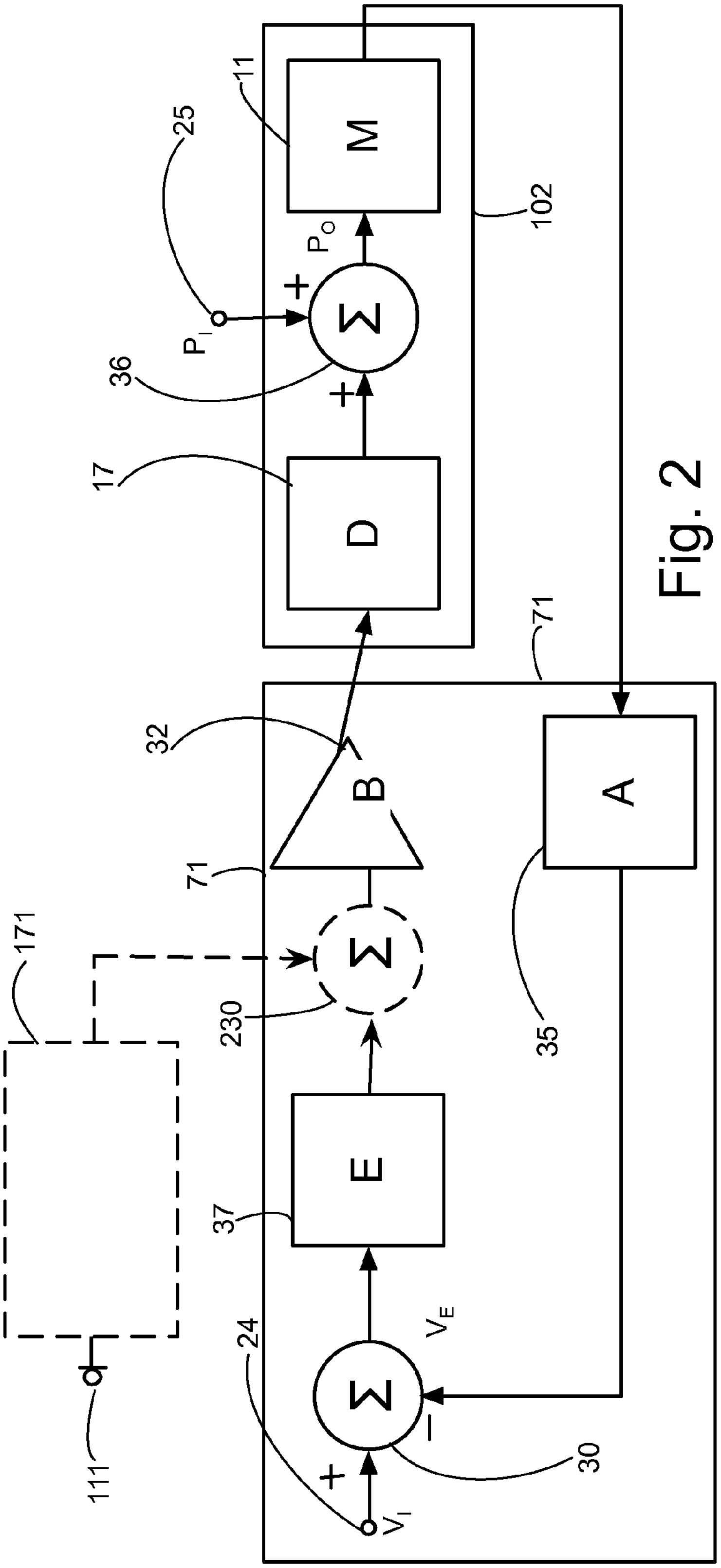
Fig. 2 Prior Art
FIG. 2 is a block diagram of an ANR earphone.

Referring to FIG. 2, there is shown a block diagram illustrating the logical arrangement of a feedback loop in an active noise reduction ANR earphone, for example as described in U.S. Pat. No. 4,455,675. A signal combiner 30 is operationally coupled to a terminal 24 for an input audio signal $V_I$ and to a feedback preamplifier 35 and is coupled to a compensator 37 which is in turn coupled to a power amplifier 32, in some embodiments, through a signal combiner 230. Power amplifier 32 is coupled to acoustic driver 17 that is acoustically coupled to the ear canal. Acoustic driver 17 and terminal 25 (which represents noise $P_I$ that enters the ear canal) are coupled by combiner 36, representing the combining of noise $P_I$ and the output of the acoustic driver. The acoustic output Po of combiner 36 is applied to a microphone 11 coupled to output preamplifier 35, which is in turn differentially coupled to signal combiner 30. The terminal 24, the signal combiner 30, the power amplifier 32, the feedback preamplifier 35, and the compensator 37 are not discussed in this specification and will be referred to collectively in subsequent views as feedback circuitry 71.

Collectively, the microphone 11, the acoustic driver 17, and the combiner 36 represent the elements of the active feedback loop that are in the front cavity 102 of the ANR earphone, that is, the acoustic volume that acoustically couples the acoustic driver and the eardrum. Some ANR earphones also have a rear cavity, that is, a cavity that is between the acoustic driver and the environment, typically separated from the front cavity by a baffle in which is mounted the acoustic driver. If present, the rear cavity may be separated from the environment by a cover which may have an opening to the environment for acoustic or pressure relief purposes.

In operation, the microphone 11 detects noise in the front cavity 102. The feedback circuitry 71 develops a feedback noise reduction signal, which is provided to amplifier 32, which amplifies the feedback noise reduction signal to provide an amplified output noise reduction signal to the acoustic driver 17. The acoustic driver 17 transduces the output noise reduction audio signal to acoustic energy, which is radiated into the front cavity.

In some implementations, the feedback loop may be supplemented by optional (as indicated by the dashed lines) feedforward noise reduction circuitry 171. The feedforward circuitry 171 receives a noise signal from feedforward microphone 111 typically positioned outside the earphone, and derives a feedforward noise reduction signal, which is summed with the feedback noise reduction signal at signal combiner 230 to provide the output noise reduction audio signal. The amplifier amplifies the output noise reduction audio signal and provides the amplified output noise reduction audio signal to the acoustic driver. Feedforward circuitry typically includes filter structures, which may include adaptive filters. Some examples of circuitry appropriate for feedforward noise reduction in earphones are described in U.S. Pat. No. 8,144,890, incorporated herein by reference in its entirety.

The front cavity is important to the operation of noise reduction earphones, because larger front cavities permit more passive attenuation, which permits more total attenuation or a lower requirement for active noise reduction, or both. In an ANR earphone, in addition to permitting more passive attenuation, the front cavity has a great effect on the operation of an active noise reduction earphone. The characteristics, such as the dimensions and geometry affect the transfer function between the acoustic driver and the eardrum, between the microphone and the acoustic driver, and between the microphone and the eardrum. Unpredictable and inconsistent transfer functions can result in feedback loop instability, which can be manifested by "squeal" which is particularly annoying with earphones because the squeal may be radiated directly into the ear canal and may be transmitted to the inner ear through the sinus cavities and through the user's bone structure. Preventing squeal can mean limiting the ANR capabilities of the ANR circuitry, for example by limiting the gain of the feedback loop or by limiting the frequency range over which the ANR circuitry operates.

Figure 3A:
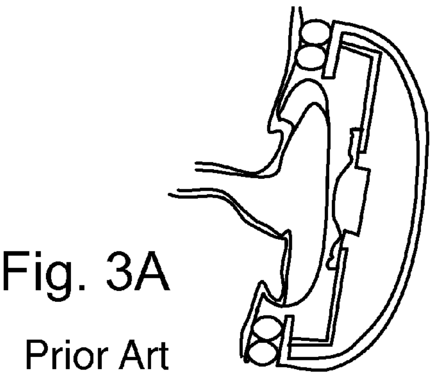
Fig. 3A Prior Art
FIGS. 3A and 3B are front cross sectional views of earphones.
Figure 3B:
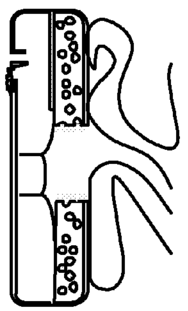
Fig. 3B Prior Art

Examples of different kinds of earphones are shown in FIGS. 3A and 3B. FIG. 3A is a circumaural earphone. In a circumaural earphone, the front cavity 102 is typically defined by the cushion which seals against the side of the head. It is therefore possible to provide a large front cavity, particularly if the volume occupied by the cushion is used, for example as in U.S. Pat. No. 6,597,792. A typical volume of a front cavity of a circumaural earphone is 114 cc. FIG. 3B is a supra-aural earphone. In a supra-aural earphone, the front cavity is defined by the cushion that seals against the external ear. While it is more difficult to provide as large a front cavity as with a circumaural earphone, the front cavity can still be made relatively large, for example 20 cc, by using the volume occupied by the cushion as part of the front cavity, for example as in U.S. Pat. No. 8,111,858.

Figure 4:
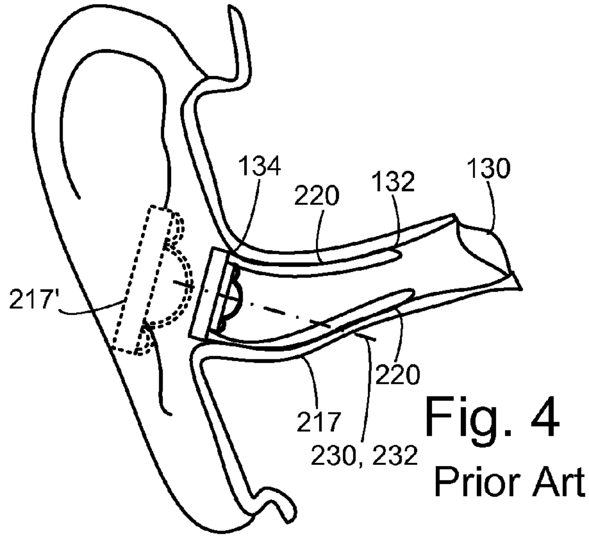
Fig. 4 Prior Art
FIG. 4 is a front cross sectional view of a prior art in-ear ANR earphone.

A diagrammatic view of a conventional in-ear ANR earphone is shown in FIG. 4. The earphone of FIG. 4 includes an acoustic driver 217 and a positioning and retaining structure 220. The positioning and retaining structure has at least four functions. It aligns the earphone in the ear when the earphone is inserted; it forms a seal with the ear canal to prevent ambient noise from entering the ear canal; it retains the earphone in position, so that if the user's head moves, the earphone remains in position; and it provides a passageway from the acoustic driver to the ear canal. Because the size and geometry of the ear canal differs widely from individual to individual, and because the walls of the ear canal are sensitive to pain and can even be damaged by portions of earphones that protrude into the ear, the positioning and aligning structures are typically made of a soft conformable material, so that the positioning and retaining structure can conform to the size and geometry of the ear canal and not cause pain or damage to the user's ear canal. Typically, the conformable material is some type of a foamed or solid elastomer, such as a silicone. To retain the earphone in the ear and to form an effective seal, the positioning and retaining structure 220 protrudes into the ear canal. However, as seen in FIG. 4, the positioning and retaining structure lies within the ear canal, which reduces the effective volume of the ear canal, which reduces the volume of the front cavity. Thus, there is a design tradeoff; if the walls of the positioning and retaining structure are too thick, they may reduce the volume of the front cavity and the cross sectional area of the path between the acoustic driver and the eardrum more than is desirable; but if the walls are too thin, the positioning and retaining structure may not adequately seal the ear canal, may not adequately prevent noise from entering the ear canal, and may not have sufficient structural strength or stability to retain the earphone in position.

Alternatively, the conformable material can be an open cell foam, which permits the volume of the foam to be used as a part of the front cavity, but open cell foam is acoustically semitransparent, so passive attenuation is compromised. Similarly, if the positioning and retaining structure protrudes too far into the ear canal, it may reduce the volume of the front cavity more than is desired; but if the positioning and retaining structure does not protrude far enough into the ear canal, it may not seal adequately, may affect the pressure gradient, and may not retain the earphone in position.

Acoustic drivers of earphones of the type shown in FIG. 4 are typically oriented so that the axis 230 of the acoustic driver 217 is substantially parallel to, or (as in this example) coincident with, the centerline 232 of the passageway from the acoustic driver to the ear canal at the position at which the acoustic driver joins the passageway. With this arrangement, the diameter of the acoustic driver is limited to the diameter of the entrance to the ear canal, of the bowl of the concha, or some other feature of the external ear. If it is desired to use a larger driver, for example, acoustic driver 217', the acoustic driver must be partially or completely unsupported mechanically. Since a large acoustic driver may have a large mass relative to other portions of the earphone, the unsupported mass may cause the earphone to be mechanically unstable in the ear. Elements 132 and 134 will be discussed below. Some elements typical of in-ear ANR earphones, such as microphones are not shown in this view.

An alternative to positioning and retaining structures that engage the ear canal is a headband, such as shown in U.S. Pat. No. 6,683,965. Headbands are considered undesirable by some users of in-ear earphones.

In addition to mechanical difficulties in positioning and retaining the earphone, the smaller front cavities of in-ear ANR earphones create additional difficulties for the design of feedback loops in ANR earphones. The front cavity includes the ear canal. Volumes and geometries of the ear canal differ substantially from individual to individual. In circumaural and supra-aural earphones, the variation in the dimensions and configuration of the ear has only a small effect on the operation of the ANR system. However, with an in-ear earphone, the ear canal is a substantial portion of the front cavity. Therefore, variations in the dimensions and geometry of the ear canal have a much larger effect on the operation of the ANR system and a blockage, kink, or constriction of the portion of the earphone that engages the ear canal also has a large effect on the operation of the ANR system. However attempting to prevent blockage, kinking, and constriction may conflict with the goal of conformability and comfort of the portion of the earphone that protrudes into the ear canal.

Figure 5:
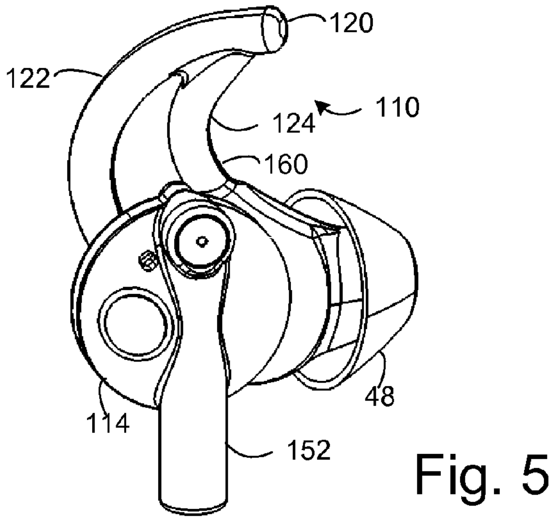
FIG. 5 is an isometric view of an in ear earphone.

FIG. 5 shows an in-ear earphone 110 that is suitable for use in an ANR system. The earphone 110 may include a stem 152 for positioning cabling and the like, an acoustic driver module 114, and a tip 160. Some earphones may lack the stem 152 but may include electronics modules (not shown) for wireless communicating with external devices. Other earphones may lack the stem and the acoustic driver module and may function as passive earplugs. The tip 160 includes a positioning and retaining structure 120, which in this example includes an outer leg 122 and an inner leg 124. The tip also includes a sealing structure 48 to seal against the opening to the ear canal to form the front cavity.

The outer leg 122 and the inner leg 124 may extend from the acoustic driver module 114. Each of the two legs is connected to the body at one end. The outer leg may be curved to generally follow the curve of the anti-helix wall at the rear of the concha. The second ends of each of the legs may be joined. The joined inner and outer legs may extend past the point of attachment to a positioning and retaining structure extremity. A suitable positioning and retaining structure is described in U.S. patent application Ser. No. 12/860,531, now U.S. Pat. No. 8,249,287, incorporated herein by reference in its entirety. In one implementation, the sealing structure 48 includes a conformable frusto-conically shaped structure that deflects inwardly when the earphone is urged into the ear canal. The structure conforms with the features of the external ear at the transition region between the bowl of the concha and the ear canal, to seal the ear canal to deter ambient noise from entering the ear canal. One such sealing structure is described in U.S. patent application Ser. No. 13/193,288, incorporated herein by reference in its entirety. The combination of the positioning and retaining structure and the sealing structure 48 provides mechanical stability. No headband or other device for exerting inward pressure to hold the earphone in place is necessary. The earphone does not need to protrude into the ear canal as far as conventional positioning and retaining structures. In some cases, the sealing structure 48 is sufficient by itself to position and retain the earphone in the ear. The positioning and retaining structure provides more mechanical stability and permits more abrupt motion of the head.

Figure 6:
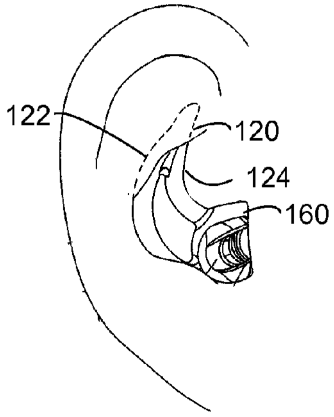
FIG. 6 is a lateral view of a portion of an earphone in an ear.

FIG. 6 is a view of a portion of the earphone of FIG. 5, in position in a user's ear. To show detail, some elements, such as the acoustic driver module 114, the sealing structure 48, and the stem 152 are omitted and the tip 160 is partially cut away. The positioning and retaining structure 120 engages with features of the outer ear so that the acoustic driver module (including the acoustic driver) is mechanically stable on a user's ear despite a substantial portion of the earphone being outside the concha of the ear when the earphone is in use. Positioning the acoustic driver module to be substantially outside the concha of the ear permits the use of a significantly larger acoustic driver than can be used in an earphone in which the acoustic driver must fit in the concha (or even partially or completely in the ear canal), without the use of a headband and without requiring the earphone to extend deep into the ear canal. The use of a larger acoustic driver permits better noise canceling performance at low frequencies, particularly in loud environments. In one implementation, a nominal 14.8 mm diameter acoustic driver is used. Typically, an acoustic driver must be less than 10 mm in diameter to fit within the concha.

Figure 7A:
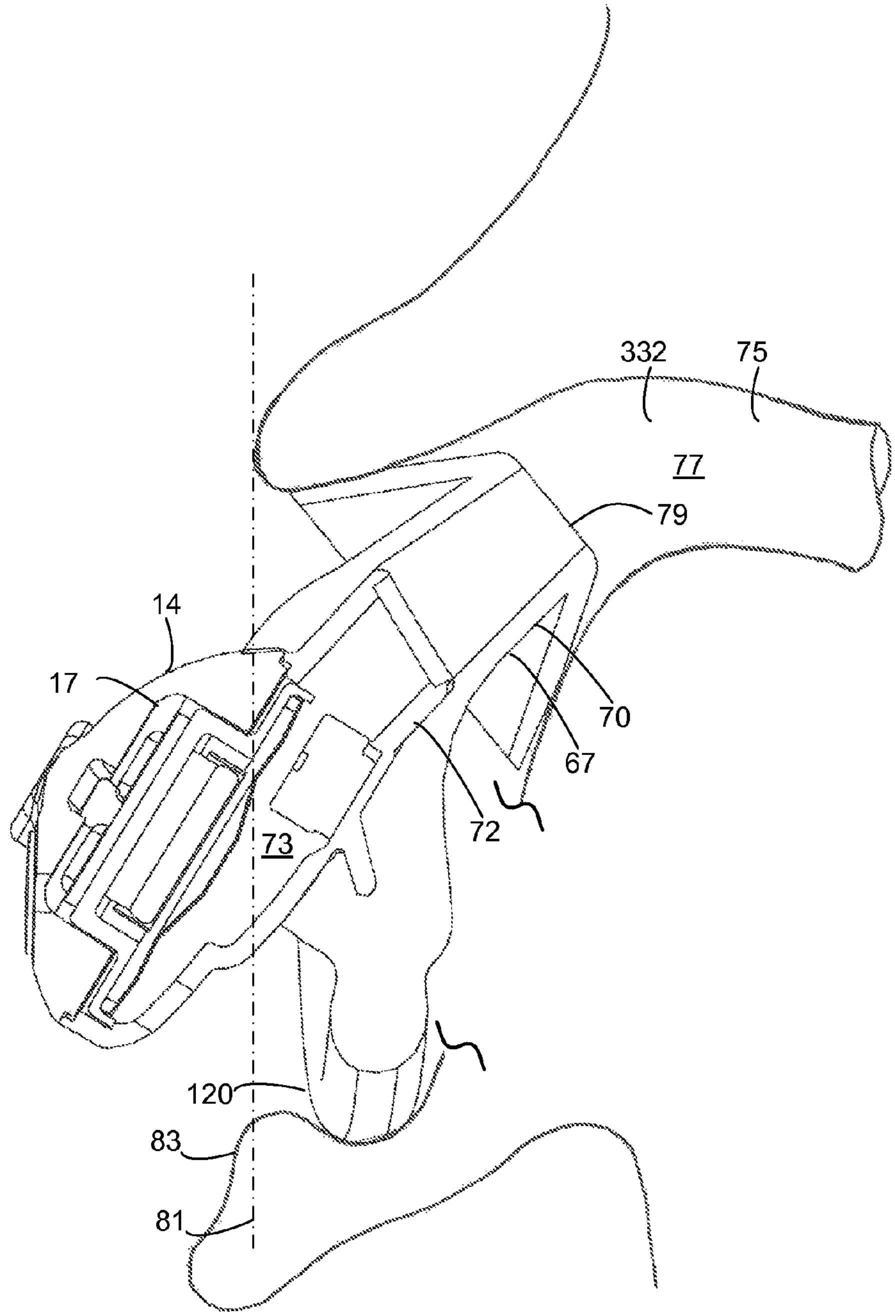
FIG. 7A is a cross sectional view of an earphone in an ear.

FIG. 7A is a cross sectional view of an actual implementation of the earphone of FIGS. 5 and 6 in place in a right ear of a user, sectioned in the transverse plane, and viewed from below. The acoustic driver 17 is acoustically coupled to the ear canal 75 by a nozzle 70, that is, a passageway that acoustically couples acoustic driver 17 and the ear canal. The combination of the sealed portion 77 of the ear canal, the space 73 in front of the diaphragm, and the nozzle 70 forms the front cavity of the earphone. In an earphone with the configuration of FIG. 4, the nozzle may include some or all of the positioning and retaining structure. The nozzle may include a stiff section 72 and a compliant section 67 and has a total length of the nozzle of about 10-12 mm. The nozzle has an oval opening with, for example, a major axis of about 5.3 mm and a minor axis of about 3.6 mm and a cross sectional area is about 15-16 $mm^2$ and volume is about 150-190 $mm^3$.

The amount of active attenuation that can be provided by an ANR earphone is limited by the impedance of the front cavity. Generally, less impedance is preferable, even if the result of reducing the impedance results in a smaller front cavity. Generally, improvements in active noise reduction due to decreased impedance more than offset any reduction in passive attenuation due to a smaller front cavity. Impedance may be reduced in a number of ways, some of which are related. Impedance is frequency dependent, and it is desirable to reduce impedance over a wide range of frequencies, or at least over the range of frequencies over which the ANR system operates. Impedance may be reduced over a broad range of frequencies, for example, by increasing the cross sectional area of the acoustic path between the acoustic driver and the eardrum, both in absolute terms and by reducing the ratio between the length of the acoustic path to the cross sectional area of the acoustic path between the acoustic driver and the eardrum and by reducing the acoustic mass of the front cavity. Of the components of the front cavity, it is difficult to achieve substantial reduction of the impedance by changing dimensions of the space (73 of FIG. 70) in front of the acoustic driver and it is impossible, or at least highly impractical, to increase the cross sectional area of the ear canal or reduce the acoustic mass of the ear canal, so the most effective way of reducing the impedance of the front cavity over a broad range of frequencies is to reduce the impedance of the nozzle 70 by increasing the cross sectional area of the nozzle 70 (which, for nozzles that do not have a uniform cross sectional area over the length of the nozzle refers to the mean cross sectional area of the nozzle or, if specified, to the minimum cross sectional area of the nozzle), by decreasing the ratio of the nozzle length to the nozzle cross sectional area, and by reducing the acoustic mass of the nozzle. Generally, an impedance with an absolute value |z| of less than $$8\times10^5\ \frac{\text{kg}}{m^4\times\text{sec}}$$

and preferably less than $$7\times10^5\ \frac{\text{kg}}{m^4\times\text{sec}}$$

at 100 Hz and less than $$8\times106\ \frac{\text{kg}}{m^4\times\text{sec}}$$

and preferably less than $$7\times10^6\ \frac{\text{kg}}{m^4\times\text{sec}}$$

at 1 kHz provides a significant improvement in active noise attenuation without significantly reducing the passive attenuation. The impedance has two components, a resistive component (DC flow resistance R) and a reactive or mass component jωM, where M is the acoustic mass, discussed below. Of these two components, the jωM term is much larger than the R term. For example, in one implementation, the absolute value or magnitude of the total impedance at 100 Hz is $$6.47\times10^5\ \frac{\text{kg}}{m^4\times\text{sec}}$$

and the mass impedance is $$6.46\times10^5\ \frac{\text{kg}}{m^4\times\text{sec}}.$$

Therefore, hereinafter, only mass impedance will be considered. Mass impedances of less than the values noted above can be obtained by providing a combination of a nozzle with an open cross sectional area A through which acoustic energy can propagate of at least 7.5 $mm^2$ and preferably 10 $mm^2$; a ratio $$\frac{l}{A}$$

(where l is the length of the nozzle) of at less than $$1000\ \frac{m}{m^2}$$

and preferably less than $$900\ \frac{m}{m^2};$$

and an acoustic mass M of less than $$1200\ \frac{\text{kg}}{m^4}$$

and preferably less than $$1100\ \frac{\text{kg}}{m^4}\ \text{where}\ M=\frac{\rho l}{A},$$

where ρ is the density of air (which if actual measurement is difficult or impossible, may be assumed to be $$1.2\ \frac{\text{kg}}{m^3}\Big).$$

In one implementation of an earphone according to FIG. 7, the cross sectional area A is about $1.4\times10^{-5}$-$1.6\times10^{-5}$ $m^2$ (14-16 $mm^2$), the ratio $$\frac{l}{A}$$

is between 625 and $$857\ \frac{m}{m^2},$$

the acoustic mass is between 750 and $$1029\ \frac{\text{kg}}{m^4},$$

the absolute value of the mass impedance is between $$4.7\times10^5\ \frac{\text{kg}}{m^4\times\text{sec}}\ \text{and}\ 6.5\times10^5\ \frac{\text{kg}}{m^4\times\text{sec}}$$

at 100 Hz and between $$4.7\times10^6\ \frac{\text{kg}}{m^4\times\text{sec}}\ \text{and}\ 6.5\times10^6\ \frac{\text{kg}}{m^4\times\text{sec}}$$

at 1 kHz.

Since the earphone has a positioning and retaining structure 120, the nozzle does not need to perform the positioning and retaining of the earphone in the user's ear and does not need to contact the ear more than is necessary to adequately seal the ear canal. The structure, dimensions, and materials of the nozzle can therefore be selected based on acoustic and comfort considerations rather than mechanical requirements. For example, the nozzle can have a cross sectional area that is at least in part as large as the cross sectional area of the widest portion of the ear canal, thereby reducing the impedance.

The earphone has several features to lessen the likelihood that the nozzle will be obstructed or blocked. Since the nozzle does not extend as far into the ear canal as conventional earphones, it is less susceptible to obstruction or blockage caused by user to user variations in the geometry and the size of the ear. The stiff section 72 resists excessive deformation of the compliant section while the compliant section permits the earphone to conform to the user's ear size and geometry without causing discomfort. In one implementation, the stiff section is made of acrylonitrile butadiene styrene (ABS), and the compliant section is made of silicone. Elements 81 and 83 will be discussed below.

Referring again to FIG. 7A, there may be a mesh screen 79 at the end of the stiff section which prevents debris from entering the acoustic driver module 14. The mesh has low acoustic resistance, less than 30 rayls, for example about 6 rayls.

Figure 7B:
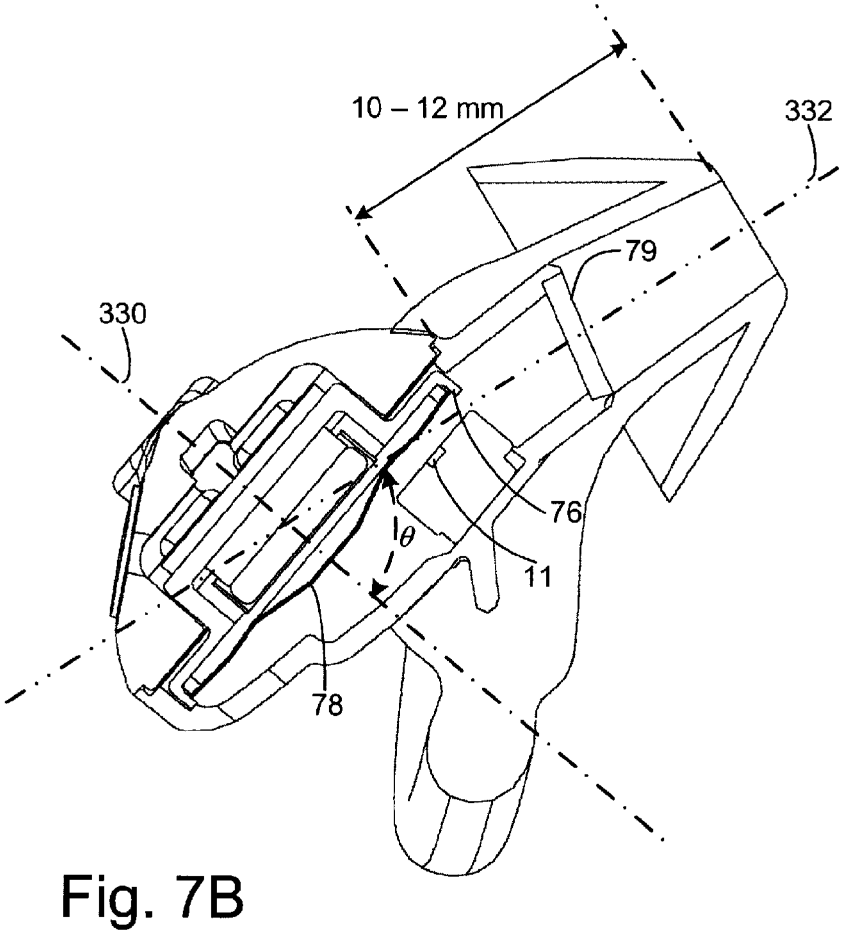
FIG. 7B is a cross sectional view of an earphone.

FIG. 7B shows the implementation of FIG. 7A, without the features of the ear of the user. One end of the nozzle is positioned close to the edge 76 of the acoustic driver diaphragm 78. The axis 330 of the acoustic driver is oriented so that a line parallel to, or coincident with, the axis 330 and that intersects centerline 332 of the nozzle at an angle $\theta>30$ degrees and preferably >45 degrees. In one implementation, $\theta\cong78$ degrees.

Figure 8A:
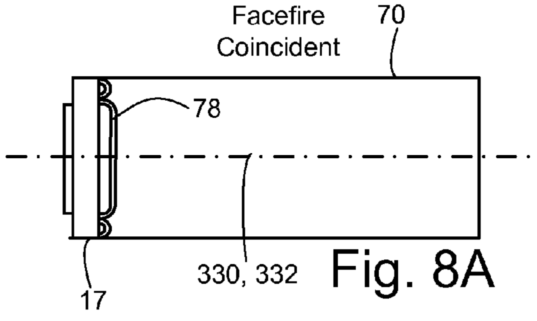
Figure 8B:
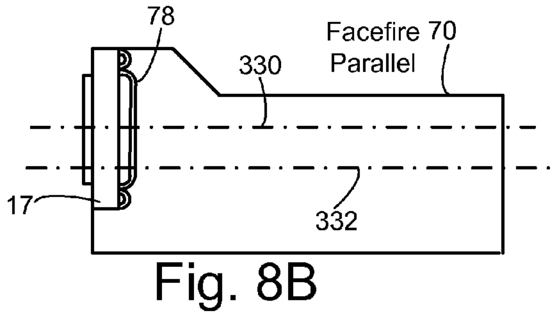
Figure 8C:
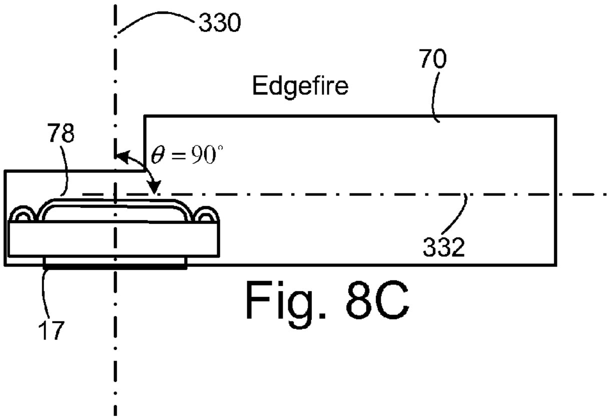
Figure 8D:
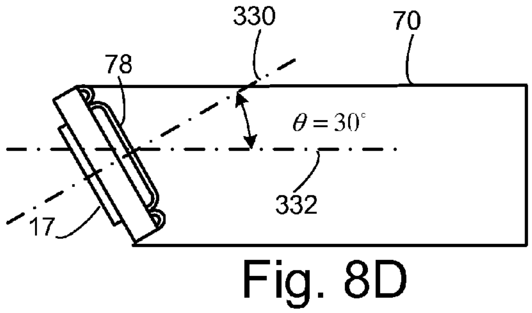

FIGS. 8A-8E are diagrammatic views illustrating the angle θ of FIG. 7. FIGS. 8A and 8B illustrate a "facefire" arrangement in which $\theta=0$ degrees. In FIG. 8A, the axis 330 of the acoustic driver and the centerline 332 of the nozzle are coincident and in FIG. 8B, the axis 330 of the acoustic driver and the centerline of the nozzle are parallel. FIG. 8C illustrates an "edgefire" arrangement in which θ=90 degrees. FIGS. 8D and 8E illustrate arrangements which are between "facefire" and "edgefire". In FIG. 8D, θ=30 degrees and in FIG. 8E, θ=45 degrees.

Referring to FIG. 9, it is desirable to place the microphone at a point 511A that is radially near the point 311 at which the diaphragm 78 is attached to the voice coil of the acoustic driver, as described in U.S. Pat. No. 8,077,874, to minimize the time delay between the radiation of acoustic energy from diaphragm 78 and the measurement of the acoustic energy by microphone 11. Generally, changing the microphone position so that the microphone is farther away from the diaphragm has a greater negative effect on the time delay than changing the microphone so that it is at a different radial position relative to the diaphragm. Placing the microphone closer to the eardrum, for example in the nozzle, provides a more gradual pressure gradient, which permits greater active noise reduction. In a conventional active noise reduction setup with a "facefire" orientation, moving the microphone closer to the eardrum to improve the pressure gradient moves the microphone away from the diaphragm, which negatively affects the time delay. Therefore changing placement of the microphone to improve pressure gradient worsens time delay, and changing placement of the microphone to improve time delay worsens the pressure gradient.

FIG. 9 shows an example of changing the location of the microphone from point 511A (above the point of attachment 311 of the voice coil and the diaphragm) to point 511B (closer to the eardrum, close to or in the nozzle). The change of location, indicated by arrow 512, has a component away from the diaphragm, indicated by arrow 523, and a component across the diaphragm, indicated by arrow 524. Location change away from the diaphragm (proportional to cos θ) negatively affects time delay. Location change across the diaphragm (proportional to sin θ) does not negatively affect time delay nearly as much as location change away from the diaphragm. In a "facefire" orientation, θ=0 degrees so that cos θ=1 and sin θ=0, so that location change toward the eardrum and toward or into the nozzle results in an equal location change away from the diaphragm. In an "edgefire" orientation, θ=90 degrees so that cos θ=0 and sin θ=1, so that location change toward the eardrum and toward or into the nozzle results in no location change away from the diaphragm. For θ=30 degrees, as shown in FIG. 5E, the amount location change across the diaphragm is 0.5 of the amount of location change away from the diaphragm, and for θ=45 degrees, a location change into the nozzle results in equal amounts of location change across and away from the diaphragm. For an actual implementation of θ=78 degrees, a location change of five units toward the eardrum into the nozzle results in location change across the diaphragm of about one unit.

Referring again to FIG. 7A, a substantial portion (indicated generally by line 81) of the acoustic driver 17 lies outside the concha of the user. The positioning and retaining structure 120 engages features 83 of the external ear to retain the earphone in place without the need for a headband.

In addition to the features that lessen the probability that the nozzle becomes blocked, the earphone may have other features to reduce negative effects from obstruction or blockage. One of the features will be discussed below.

Figure 10A:
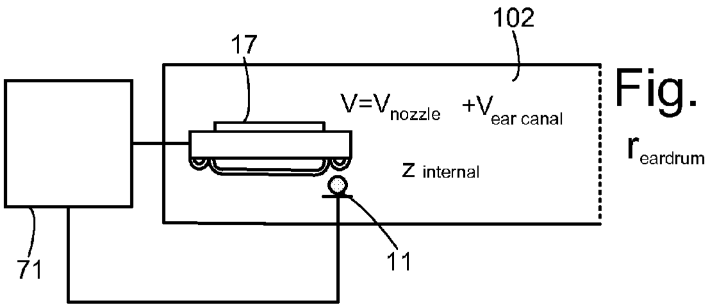
FIGS. 10A and 10B are diagrammatic views of an earphone.
Figure 10B:
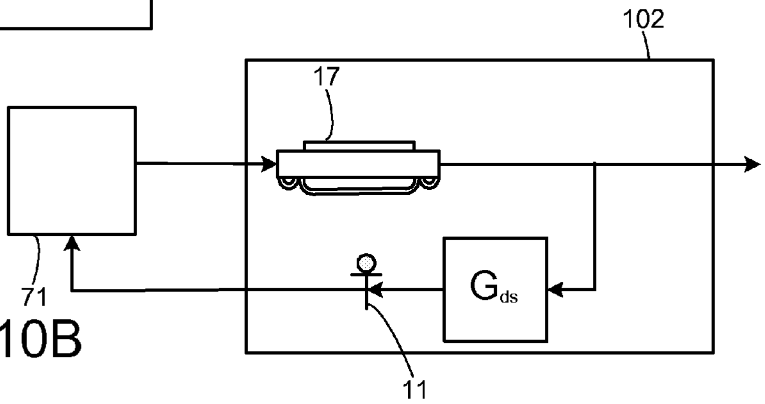

FIGS. 10A and 10B illustrate another feature of the earphone. FIG. 10A shows the feedback loop of FIG. 2, as implemented in the ANR earphone of FIGS. 5 and 7. The front cavity 102 of the ANR earphone in which the feedback loop is employed includes an acoustic volume v, which includes the volume $v_{nozzle}$ of the nozzle 70 of FIG. 5 plus the volume $V_{ear\ canal}$ of the user's ear canal. The front cavity may also be characterized by an acoustic resistance representing the acoustic resistance $r_{eardrum}$ of the eardrum. Together, $r_{eardrum}$ and volume v form an impedance $z_{internal}$. As depicted in FIG. 10B, the geometry and dimensions of the front cavity and the resistance of the eardrum are among the factors which determine a transfer function $G_{ds}$, that is, the transfer function from the acoustic driver 17 to the microphone 11.

Figure 11A:
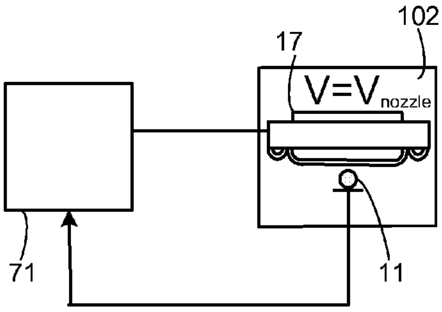
FIGS. 11A and 11B are diagrammatic views of earphones.
Figure 11B:
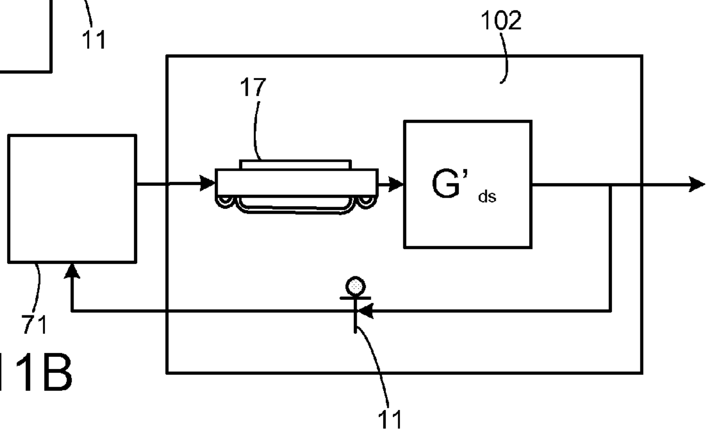

If the geometry, dimensions, acoustic resistance, or impedance are different than the geometry, dimensions, acoustic resistance, or impedance that was used in designing the feedback loop (for example as in FIG. 11A in which the nozzle has been blocked so that $v \neq v_{earpiece}+v_{earcanal}$, for example $v=V_{earpiece}$), the transfer function may be some other function, for example $G'_{ds}$ of FIG. 11B, which may cause the feedback loop to become unstable or to perform poorly. For example, FIGS. 12A and 12B show, respectively, magnitude (97A) and phase (98A) of the transfer function Gds compared with the magnitude (97B) and phase (98B) of a transfer function with the nozzle blocked. The two curves diverge by about 20 dB at 1 kHz and by 45 to 90 degrees between 1 kHz and 3 kHz.

FIGS. 13A and 13B show a configuration that lessens the likelihood that an obstruction or blockage of the nozzle will alter the transfer function enough to cause instability in the feedback loop. In the configuration of FIG. 13A, the front cavity 102 is coupled to the environment by a shunt 80 with an impedance $z_{external}$. The shunt lessens the likelihood that an obstruction or blockage of the nozzle would cause an instability in the feedback loop. The impedance Z external should be low at low frequencies and higher than $z_{internal}$ at high frequencies. The shunt may be an opening to the environment with an impedance-providing structure in the opening. The impedance-providing structure could be a resistive screen 82 as shown in FIG. 13A. Alternatively, the shunt may be provided by forming acoustically resistive holes in the shell of the earphone or by an insert with holes formed in the insert. The shunt results in the acoustic driver being acoustically coupled to the environment by impedance $z_{external}$ and to the feedback circuitry 61 by transfer function Gds as shown in FIG. 13B.

Figure 14:
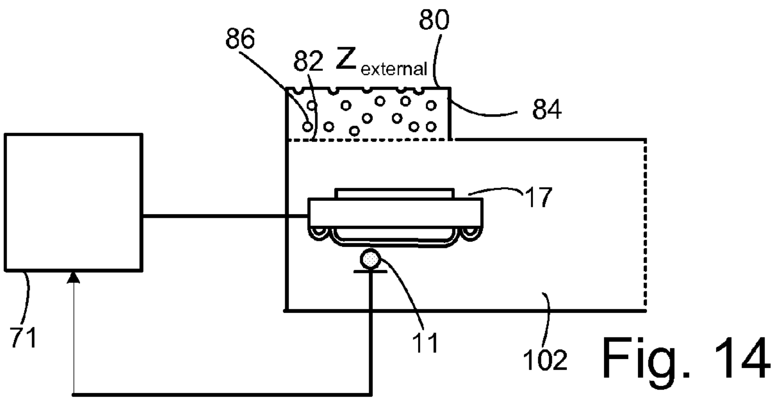
FIG. 14 is a diagrammatic view of an of an earphone.

In FIG. 14, the shunt 80 has the opening and the screen 82 of FIG. 12. Additionally, the opening 80 and screen 82 are coupled to the environment by a tube 84 filled with foam 86. The tube provides for more precision in determining the impedance $z_{external}$, and the foam damps resonances that may occur in the tube. Other configurations are possible; for example, the resistive screen may be at the exterior end 88 of the tube 84, or there may be resistive screens in the opening 80 and the exterior end 88 of the tube 84.

Figure 15A:
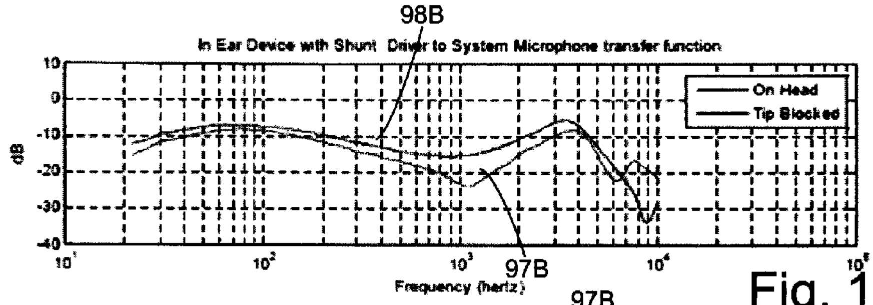
FIGS. 15A and 15B are plots of amplitude and phase, respectively, vs. frequency.
Figure 15B:
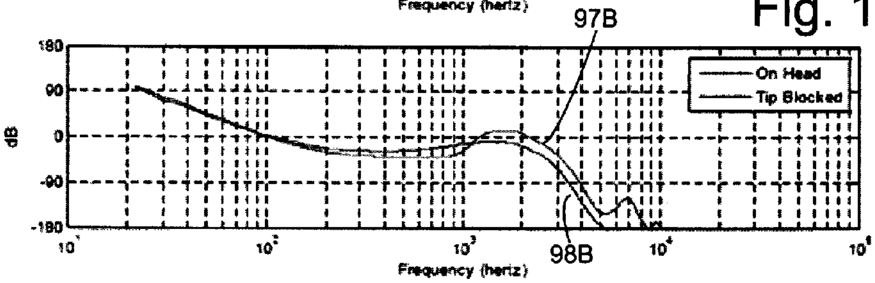

FIGS. 15A and 15B show, respectively, the magnitude and phase of the transfer function $G_{ds}$ of an earphone according to FIG. 9 with the nozzle unblocked (curve 97B) and blocked (curve 98B). The curves diverge much less than the curves of FIG. 8.

Figure 16:
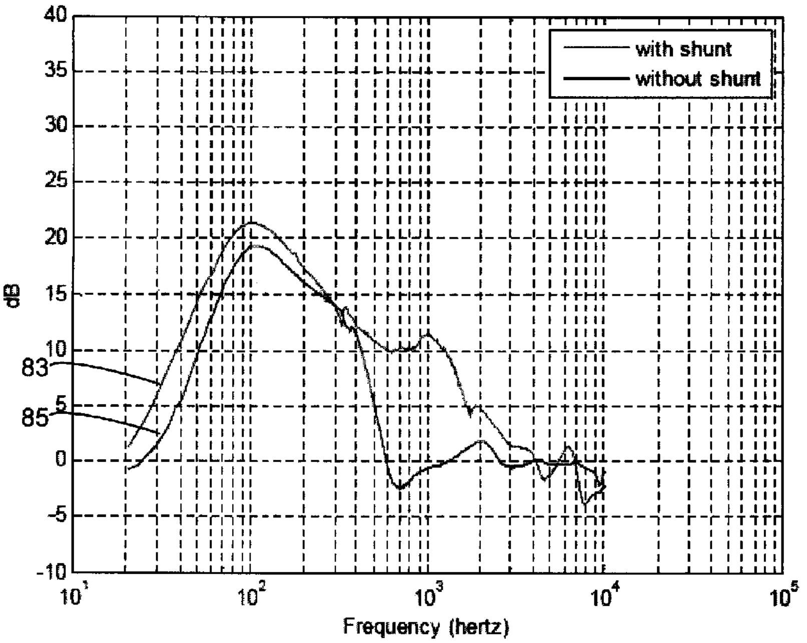
FIG. 16 is a plot of amplitude vs. frequency.

FIG. 16 shows the total active cancellation at the system microphone 11 of previous figures with and without the shunt. Without the shunt, represented by curve 83, there is a pronounced drop to less than 0 dB between about 300 Hz and 800 Hz. With the shunt, represented by curve 85, the dropoff is eliminated, so that between about 700 Hz and 1 kHz, there is 10 dB or more difference in between the two configurations.

Figure 17:
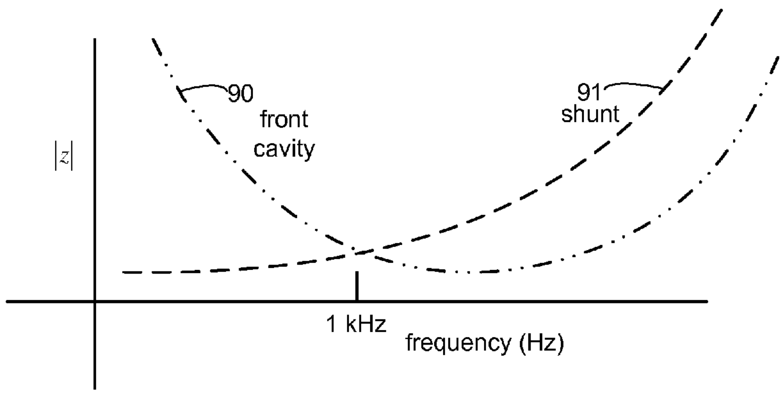
FIG. 17 is a plot of impedance vs. frequency.

FIG. 17 shows an example of the effect of the shunt 80. FIG. 17 shows the magnitude |z| as a function of frequency.

Figure 18:
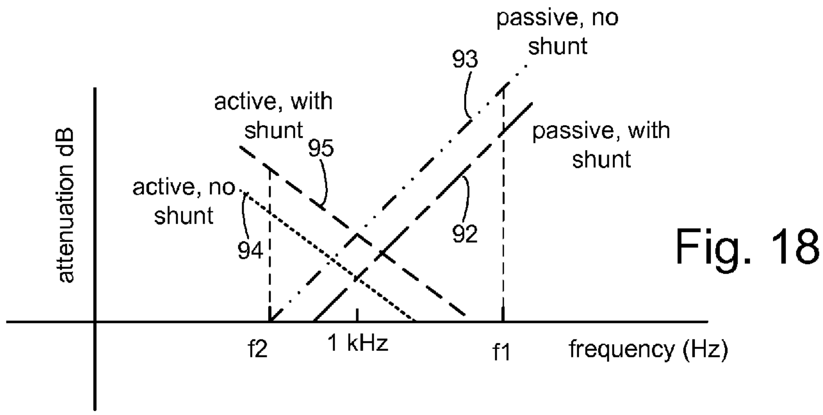
FIG. 18 is a plot of attenuation vs. frequency.

Curve 90 represents the magnitude of the impedance of the front cavity. At low frequencies, below, for example, about 100 Hz, the front cavity impedance is very high and the impedance reaches a minimum at about 1 kHz and increases at higher frequencies. Curve 91 represents the magnitude of the impedance of the shunt, $|z_{external}|$. At low frequencies, below about 1 kHz, the impedance of the shunt is very low. After 1 kHz, the impedance increases more rapidly than the impedance of the front cavity and eardrum. Thus, at frequencies below 1 kHz, the impedance of the shunt predominates and at frequencies above 1 kHz, the impedance of the front cavity predominates Employing the shunt 80 necessitates a tradeoff between passive noise attenuation and active noise attenuation. The tradeoff is illustrated in FIG. 18, which is a plot of attenuation in dB (where a more positive value on the vertical axis indicates greater attenuation) vs. frequency. In FIG. 18, curve 92 represents the passive attenuation provided by the earphone with the shunt and curve 93 represents the passive attenuation provided by the earphone without the shunt. In the frequency range above about 1 kHz in which passive attenuation is dominant, at any given frequency, for example $f_1$, the passive attenuation provided by the earphone without the shunt is greater than the passive attenuation with the shunt. Curve 94 represents the active attenuation that can be provided by the earphone with the shunt and curve 95 represents the active attenuation that can be provided by the earphone without the shunt. In the frequency range below about 1 kHz, where active attenuation is dominant, at any given frequency, for example $f_2$, the attenuation than can be provided by the earphone with the shunt is greater than the attenuation that can be provided by the earphone without the shunt.

Looked at in terms of total attenuation, the earphone without the shunt provides less attenuation at lower frequencies and more attenuation at higher frequencies, while the reverse is true of the earphone with the shunt so there may not be a significant difference in the total attenuation provided. However, in addition to the attenuation provided, and the better stability if the nozzle becomes blocked or obstructed, there may be other reasons why the structure of FIGS. 13 and 14 is advantageous. For example, the shunt provides a more natural sound for ambient sounds and for sound originating with the user (for example, the user hearing his/her own voice conducted to the ear through the ear canal, through the bone structure, and through the sinus cavities). Without the shunt, the earphone acts like an earplug, so that the ambient sound that reaches the eardrum is "boomy" and has a "stuffy" sound. With the shunt, the ambient sound and the sound originating with the user has a more natural sound.

Numerous uses of and departures from the specific earphone and techniques disclosed herein may be made without departing from the inventive concepts. Consequently, the invention is to be construed as embracing each and every novel feature and novel combination of features disclosed herein and limited only by the spirit and scope of the appended claims.

What is claimed is:

1. An active noise reduction (ANR) earphone, comprising:

an acoustic driver configured to deliver acoustic energy into a front cavity, the front cavity including a first volume of space inside the earphone and into which the acoustic driver delivers the acoustic energy, a second volume of space inside the ear canal of a user, and a nozzle section coupling the first and second volumes;

a tip for coupling the earphone to the ear of the user, the tip including at least a portion of the nozzle section coupling the first volume of the front cavity to the second volume of the front cavity; and active noise reduction circuitry comprising a feedback microphone acoustically coupled to the first volume of the front cavity, for detecting noise in the front cavity;

feedback circuitry responsive to the feedback microphone for providing a feedback noise cancelling audio signal into the front cavity;

a feed-forward microphone acoustically coupled to ambient space outside the housing;

feed-forward circuitry responsive to the feed-forward microphone for providing a feed-forward noise canceling audio signal into the front cavity; and wherein the acoustic driver is configured to transduce an output noise canceling audio signal comprising the feedback noise canceling audio signal and the feed-forward noise canceling audio signal into acoustic energy;

wherein the nozzle is oriented and shaped to control the acoustic impedance of the nozzle, such that at least one of the cross-sectional area of the nozzle, the ratio of the nozzle length to the nozzle cross sectional area, or the acoustic mass of the nozzle causes the impedance of the nozzle to be below a threshold that varies over the operating range of the active noise reduction circuitry.

2. The earphone of claim 1, wherein the nozzle section is formed of a rigid material.

3. The earphone of claim 1, wherein the nozzle is configured to penetrate at least partially into the opening of the ear canal of a user.

4. The earphone of claim 3, wherein the ear tip is at least partially formed of a compliant material and covers at least the portion of the nozzle that penetrates into the opening of the ear canal of the user.

5. The earphone of claim 1, wherein the nozzle comprises a rigid portion and a compliant portion.

6. The earphone of claim 5, wherein the nozzle comprises a frusto-conically shaped structure for engaging the area of transition between the ear canal and the bowl of the concha and acoustically coupling the ear canal with the nozzle.

7. The earphone of claim 1, wherein the tip is configured to form a seal near the area of transition between the ear canal and the bowl of the concha.

8. The earphone of claim 1, wherein the tip includes a frusto-conically-shaped portion formed of a compliant material for acoustically sealing the area of transition between the ear canal and the bowl of the concha.

9. The earphone of claim 7 or 8, wherein the tip is configured to terminate near the entrance of the ear canal such that it does not substantially penetrate into the ear canal.

10. The earphone of claim 1, wherein the tip is removable from the housing.

11. The earphone of claim 10, wherein the tip includes a frusto-conically-shaped portion formed of a compliant material for acoustically sealing the area of transition between the ear canal and the bowl of the concha, and is interchangeable with ear tips having differently-sized frustro-conically-shaped portions.

12. The earphone of claim 10, wherein the tip includes a leg engaging the outer ear for positioning and retaining the earphone in the ear of a user, and is interchangeable with tips having differently-sized retaining legs.

13. The earphone of claim 1,
wherein the acoustic driver is oriented so that a line parallel to, or coincident with, an axis of the acoustic driver intersects a centerline of the nozzle at angle θ>±30 degrees.

14. The earphone of claim 1,
wherein the absolute value of the mass impedance |z| of the nozzle section is $$8.0\times 10^{6}\frac{kg}{m^{4}sec}$$

or less at 1 kHz.

15. The earphone of claim 1,
wherein the absolute value of the mass impedance |z| of the nozzle section is $$800\times 10^{3}\ \frac{\text{kg}}{m^{4}\ \text{sec}}$$

or less at 100 Hz.

16. The earphone of claim 1,
wherein the nozzle section has an acoustic mass $$1200\ \frac{\text{kg}}{m^{4}}$$

or less, where $$M=\frac{\rho l}{A},$$

ρ is the density of air, A is the open cross sectional area of the nozzle section and l is the length of the nozzle section.

17. The earphone of claim 1, further comprising structure engaging the outer ear for positioning and retaining the earphone in the ear.

18. The earphone of claim 1, wherein the acoustic driver has a nominal diameter of greater than 10 mm.

19. The earphone of claim 15, where the acoustic driver has a nominal diameter of greater than 14 mm.

20. The earphone of claim 1, wherein the earphone is configured so that a portion of the acoustic driver is within the concha of a user and another portion of the acoustic driver is outside the concha of the user when the earphone is in position.

21. The earphone of claim 1, wherein the feedback microphone is radially positioned intermediate a point at which a diaphragm of the acoustic driver is attached to a voice coil of the acoustic driver and an edge of the diaphragm.

22. The earphone of claim 1, wherein the feedback microphone is positioned at the intersection of a module supporting the acoustic driver and the nozzle section.

23. The earphone of claim 1, wherein
the front cavity is coupled to a first sound-radiating surface of the acoustic driver; and the earphone further comprises
a rear cavity coupled to a second sound-radiating surface of the acoustic driver and defining an enclosed acoustic volume, including a port coupling the enclosed acoustic volume to the ambient space around the earphone.

24. An active noise reduction (ANR) earphone, comprising:
an acoustic driver configured to deliver acoustic energy into a front cavity,
the front cavity including a first volume of space inside the earphone and into which the acoustic driver delivers the acoustic energy, a second volume of space inside the ear canal of a user, and a nozzle section coupling the first and second volumes,
wherein the acoustic driver is oriented so that a line parallel to, or coincident with, an axis of the acoustic driver intersects a centerline of the nozzle section at an angle θ>±30 degrees, and
the absolute value of the mass impedance |z| of the nozzle section is $$8.0\times 10^{6}\frac{kg}{m^{4}sec}$$

or less at 1 kHz;
a tip for coupling the earphone to the ear of the user,
the tip including at least a portion of the nozzle section coupling the first volume of the front cavity to the second volume of the front cavity; and
active noise reduction circuitry comprising
a feedback microphone acoustically coupled to the first volume of the front cavity, for detecting noise in the front cavity;
feedback circuitry responsive to the feedback microphone for providing a feedback noise cancelling audio signal into the front cavity;
a feed-forward microphone acoustically coupled to ambient space outside the housing;
feed-forward circuitry responsive to the feed-forward microphone for providing a feed-forward noise canceling audio signal into the front cavity; and
wherein the acoustic driver is configured to transduce an output noise canceling audio signal comprising the feedback noise canceling audio signal and the feed-forward noise canceling audio signal into acoustic energy.

25. An active noise reduction (ANR) earphone, comprising:
an acoustic driver configured to deliver acoustic energy into a front cavity,
the front cavity including a first volume of space inside the earphone and into which the acoustic driver delivers the acoustic energy, a second volume of space inside the ear canal of a user, and a nozzle section coupling the first and second volumes,
wherein the acoustic driver is oriented so that a line parallel to, or coincident with, an axis of the acoustic driver intersects a centerline of the nozzle section at an angle θ>±30 degrees, and
the absolute value of the mass impedance |z| of the nozzle section is $$800\times 10^{3}\frac{kg}{m^{4}sec}$$

or less at 100 Hz;
a tip for coupling the earphone to the ear of the user,
the tip including at least a portion of the nozzle section coupling the first volume of the front cavity to the second volume of the front cavity; and active noise reduction circuitry comprising a feedback microphone acoustically coupled to the first volume of the front cavity, for detecting noise in the front cavity;

feedback circuitry responsive to the feedback microphone for providing a feedback noise cancelling audio signal into the front cavity;

a feed-forward microphone acoustically coupled to ambient space outside the housing;

feed-forward circuitry responsive to the feed-forward microphone for providing a feed-forward noise canceling audio signal into the front cavity; and wherein the acoustic driver is configured to transduce an output noise canceling audio signal comprising the feedback noise canceling audio signal and the feed-forward noise canceling audio signal into acoustic energy.

26. An active noise reduction (ANR) earphone, comprising:

an acoustic driver configured to deliver acoustic energy into a front cavity, the front cavity including a first volume of space inside the earphone and into which the acoustic driver delivers the acoustic energy, a second volume of space inside the ear canal of a user, and a nozzle section coupling the first and second volumes, wherein the acoustic driver is oriented so that a line parallel to, or coincident with, an axis of the acoustic driver intersects a centerline of the nozzle section at an angle $\theta > \pm 30$ degrees, and the nozzle section has an acoustic mass M of $$1200 \frac{\text{kg}}{\text{m}^4}$$

or less, where $$M = \frac{\rho l}{A},$$

ρ is the density of air, A is the open cross sectional area of the nozzle section and l is the length of the nozzle section;

a tip for coupling the earphone to the ear of the user, the tip including at least a portion of the nozzle section coupling the first volume of the front cavity to the second volume of the front cavity; and active noise reduction circuitry comprising a feedback microphone acoustically coupled to the first volume of the front cavity, for detecting noise in the front cavity;

feedback circuitry responsive to the feedback microphone for providing a feedback noise cancelling audio signal into the front cavity;

a feed-forward microphone acoustically coupled to ambient space outside the housing;

feed-forward circuitry responsive to the feed-forward microphone for providing a feed-forward noise canceling audio signal into the front cavity; and wherein the acoustic driver is configured to transduce an output noise canceling audio signal comprising the feedback noise canceling audio signal and the feed-forward noise canceling audio signal into acoustic energy.

* * * * *